(12) United States Patent
Oomori

(10) Patent No.: US 12,150,712 B2
(45) Date of Patent: Nov. 26, 2024

(54) CORNEAL ENDOTHELIAL CELL IMAGING APPARATUS, METHOD OF CONTROLLING SAME, AND RECORDING MEDIUM

(71) Applicant: Topcon Corporation, Tokyo (JP)

(72) Inventor: Kazuhiro Oomori, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 515 days.

(21) Appl. No.: 17/572,642

(22) Filed: Jan. 11, 2022

(65) Prior Publication Data

US 2022/0125308 A1   Apr. 28, 2022

Related U.S. Application Data

(63) Continuation of application No. PCT/JP2020/033390, filed on Sep. 3, 2020.

(60) Provisional application No. 62/898,643, filed on Sep. 11, 2019.

(51) Int. Cl.
 *A61B 3/135* (2006.01)
 *A61B 3/00* (2006.01)

(52) U.S. Cl.
 CPC ............ *A61B 3/135* (2013.01); *A61B 3/0008* (2013.01)

(58) Field of Classification Search
 CPC ......... A61B 3/135; A61B 3/0008; A61B 3/14; A61B 3/117
 USPC ........................................................ 351/214
 See application file for complete search history.

(56) References Cited

U.S. PATENT DOCUMENTS

| 7,331,669 B2 | 2/2008 | Elsner |
| 7,831,106 B2 | 11/2010 | Elsner et al. |
| 8,237,835 B1 | 8/2012 | Muller |

(Continued)

FOREIGN PATENT DOCUMENTS

| JP | 2014-18226 A | 2/2014 | |
| JP | 2014239812 A | * 12/2014 | ............. A61B 3/107 |
| JP | 2016101235 A | * 6/2016 | |

(Continued)

OTHER PUBLICATIONS

International Search Report and Written Opinion mailed on Nov. 10, 2020, received for PCT Application PCT/JP2020/033390, Filed on Sep. 3, 2020, 8 pages including English Translation.

*Primary Examiner* — Mohammed A Hasan
(74) *Attorney, Agent, or Firm* — XSENSUS LLP

(57) ABSTRACT

A corneal endothelial cell imaging apparatus includes an irradiation system, a light receiving system, and a controller. The irradiation system includes a spatial light modulator modulating light from a light source, and is configured to irradiate slit-shaped illumination light toward a cornea by modulating the light using the spatial light modulator. The light receiving system is arranged obliquely to the irradiation system and includes an image sensor receiving reflected light from the cornea. The controller is configured to control the spatial light modulator so as to irradiate the illumination light onto an illumination region on the cornea, and is configured to control the image sensor to set an opening range on a light receiving surface corresponding to the illumination region on the cornea and to capture a light receiving result of reflection component from a corneal endothelium obtained by a light receiving element in the set opening range.

17 Claims, 7 Drawing Sheets

(56) References Cited

U.S. PATENT DOCUMENTS 8,488,895 B2    7/2013   Muller et al.
2014/0016094 A1   1/2014   Sakashita

FOREIGN PATENT DOCUMENTS

JP       2017158726 A  *  9/2017
WO       WO-03039332 A2  *  5/2003   ............... A61B 3/12

* cited by examiner

CORNEAL ENDOTHELIAL CELL IMAGING APPARATUS, METHOD OF CONTROLLING SAME, AND RECORDING MEDIUM

CROSS-REFERENCE TO RELATED APPLICATIONS

The present application is a continuation application of International Patent Application No. PCT/JP2020/033390, filed Sep. 3, 2020, which claims priority to U.S. Provisional Application No. 62/898,643, filed Sep. 11, 2019. The contents of these applications are incorporated herein by reference in their entirety.

FIELD

The disclose relates to a corneal endothelial cell imaging apparatus, a method of controlling the same, and a recording medium.

BACKGROUND

Corneal endothelial cell imaging apparatuses can irradiate slit light onto a subject's eye from an oblique direction and can receive light having a reflection component from a corneal endothelial cell among reflected light from a cornea to image the corneal endothelial cell. In the corneal endothelial cell imaging apparatuses, clear images of the corneal endothelial cell can be obtained by precisely performing position matching of the imaging optical system with reference to the subject's eye in a direction of the optical axis and by focusing on the corneal endothelium (Japanese Unexamined Patent Application Publication No. 2014-239812, Japanese Unexamined Patent Application Publication No. 2014-018226, Japanese Unexamined Patent Application Publication No. 2017-158726).

Such a corneal endothelial cell imaging apparatus, for example, specifies a size or a shape of the corneal endothelial cells by analyzing the acquired image of the corneal endothelial cells, and generates information based on the specified size or the specified shape as information for diagnosing the health of the cornea. In this case, an image of a wider range of the corneal endothelial cells is acquired in order to improve the reliability of the generated information.

For example, Japanese Unexamined Patent Application Publication No. 2014-239812 and the Japanese Unexamined Patent Application Publication No. 2014-018226 disclose a method of projecting fixation target at different positions on the cornea while changing presentation positions of the fixation target using a fixation projection system to acquire a plurality of images of the corneal endothelial cell. In a method disclosed in Japanese Unexamined Patent Application Publication No. 2014-239812, a panoramic image is generated by synthesizing the acquired images. In a method disclosed in Japanese Unexamined Patent Application Publication No. 2014-018226, the acquired images are simultaneously displayed on a display screen.

For example, Japanese Unexamined Patent Application Publication No. 2017-158726 discloses a method of generating a synthetic image by synthesizing two or more images obtained by changing the position of the slit by moving a slit member.

SUMMARY

One aspect of some embodiments is a corneal endothelial cell imaging apparatus, including: an irradiation system including a spatial light modulator modulating light from a light source, and configured to irradiate slit-shaped illumination light toward a cornea of a subject's eye by modulating the light from the light source using the spatial light modulator; a light receiving system arranged obliquely to the irradiation system and including an image sensor receiving reflected light from the cornea; and a controller configured to control the spatial light modulator so as to irradiate the illumination light onto an illumination region on the cornea, and configured to control the image sensor to set an opening range on a light receiving surface corresponding to the illumination region on the cornea and to capture a light receiving result of reflection component from a corneal endothelium obtained by a light receiving element in the set opening range.

Another aspect of some embodiments is a method of controlling a corneal endothelial cell imaging apparatus including: an irradiation system including a spatial light modulator modulating light from a light source, and configured to irradiate slit-shaped illumination light toward a cornea of a subject's eye by modulating the light from the light source using the spatial light modulator; and a light receiving system arranged obliquely to the irradiation system and including an image sensor receiving reflected light from the cornea. The method of controlling the corneal endothelial cell imaging apparatus includes an irradiation system control step of controlling the spatial light modulator so as to irradiate the illumination light onto an illumination region on the cornea; and a light receiving system control step of controlling the image sensor to set an opening range on a light receiving surface corresponding to the illumination region on the cornea and to capture a light receiving result of reflection component from a corneal endothelium obtained by a light receiving element in the set opening range.

Yet another aspect of some embodiments is a non-transitory computer readable recording medium storing a program of causing a computer to execute each step of the method of controlling the corneal endothelial cell imaging apparatus described above.

DETAILED DESCRIPTION

Figure 1:
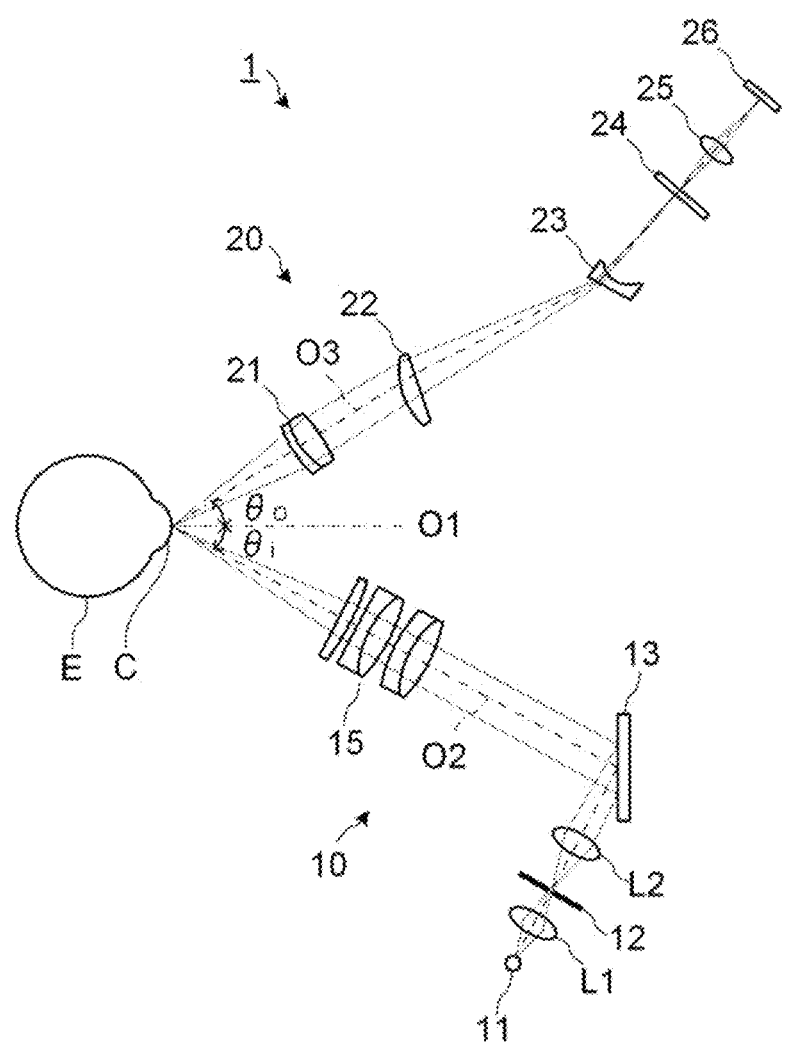
FIG. 1 is a schematic diagram illustrating an example of a configuration of an optical system of a corneal endothelial cell imaging apparatus according to embodiments.

In order to diagnose the health of the cornea with accuracy, it is required to easily acquire a higher quality image of corneal endothelial cell(s) in a wider range.

However, in the method disclosed in Japanese Unexamined Patent Application Publication No. 2014-239812 and Japanese Unexamined Patent Application Publication No. 2014-018226, a plurality of images is acquired by changing the presentation position of the fixation target. Thereby, it takes at least 10 to 20 seconds to acquire each image. Therefore, during this process, the eye may move, which may make it difficult to perform position matching on the plurality of acquired images or may require reacquisition of images. Thus, it is not easy to acquire high quality images with a wide field of view. Further, in the method disclosed in Japanese Unexamined Patent Application Publication No. 2017-158726, the optical system becomes more complicated and the size of the apparatus becomes larger.

According to some embodiments according to present invention, a new technique for easily acquiring high quality images of the corneal endothelial cell(s) can be provided with a simple configuration.

Referring now to the drawings, exemplary embodiments of a corneal endothelial cell imaging apparatus, a method of controlling the corneal endothelial cell imaging apparatus, and a program according to the present invention are described below. Any of the contents of the documents cited in the present specification and arbitrary known techniques may be applied to the embodiments below.

In the following description, the left/right direction viewed from a subject is regarded as the X direction, the up/down direction is regarded as the Y direction, and the depth direction of an optical system (optical axis direction, front/back direction) viewed from the subject is regarded as the Z direction. The X and Y directions may be referred to as the XY direction.

A corneal endothelial cell imaging apparatus according to embodiments can irradiate slit-shaped illumination light toward a subject's eye by modulating light from a light source, and can receive reflected light from a cornea of the subject's eye irradiated with the illumination light to image (photograph) the corneal endothelial cell(s). The corneal endothelial cell imaging apparatus includes an irradiation system having a spatial light modulator and a light receiving system having an image sensor. The spatial light modulator guides the illumination light to a predetermined illumination region on the cornea by modulation the light from the light source. The image sensor receives the reflected light from the cornea. The image sensor is controlled so as to capture (fetch) a light receiving result obtained by a light receiving element in an opening range on the light receiving surface of the reflected light corresponding to the illumination region of the illumination light on the cornea.

This allows to efficiently receive the reflection component(s) from the corneal endothelium without being affected by unnecessary reflection component(s) (e.g., the reflection component(s) from the corneal epithelium).

Further, the spatial light modulator sequentially moves the illumination region on the cornea by modulating the light from the light source. In this case, the image sensor is controlled so as to sequentially set the opening range on the light receiving surface of the reflected light, in synchronization with the movement of the illumination region of the illumination light, and to sequentially capture the light receiving results obtained by the light receiving elements in the opening range, for example, using a rolling shutter method.

This allows to image the corneal endothelial cell(s) at high speed with a simple configuration. In addition, by moving the opening range on the light receiving surface in synchronization with the movement of the illumination region of the illumination light on the cornea, this allows to efficiently receive the reflection component(s) from the corneal endothelium without being affected by unnecessary reflection component(s) (e.g., the reflection component(s) from the corneal epithelium).

A method of controlling the corneal endothelial cell imaging apparatus according to the embodiments includes one or more steps for realizing the processing executed by a processor (computer) in the corneal endothelial cell imaging apparatus according to the embodiments. A program according to the embodiments causes the processor to execute each step of the method of controlling the corneal endothelial cell imaging apparatus according to the embodiments. A recording medium according to the embodiments is a non-transitory recording medium (storage medium) on which the program according to the embodiments is recorded.

The corneal endothelial cell imaging apparatus includes a base, a base unit provided above the base, and a measurement head that can be moved in the X, Y, and Z directions relative to the base unit. The measurement head is provided with an optical system for imaging (photographing) the corneal endothelial cell(s) of the subject's eye. The base is provided with a supporting member that holds a chin support unit and a forehead rest unit. For example, using a known alignment method, alignment of the optical system to the subject's eye can be performed by moving the measurement head with respect to the subject's eye with the chin on the chin support unit and the forehead on the forehead rest unit (see Japanese Unexamined Patent Application Publication No. 2014-239812).

In the following, a case where the corneal endothelial cell imaging apparatus according to the embodiments acquires an image of the corneal endothelial cell(s) using an optical scanner as the spatial light modulator will be described. In some embodiments, the corneal endothelial cell imaging apparatus acquires a plurality of images of the corneal endothelial cell(s) with different imaging regions, and synthesizes these images to obtain an image of the corneal endothelial cell(s) with a wide field of view as a panoramic image.

[Optical System]

FIG. 1 shows an example of a configuration of an optical system of a corneal endothelial cell imaging apparatus according to embodiments. FIG. 1 represents the example of the configuration of the optical system in case of performing critical illumination on the corneal endothelial cells. The optical system shown in FIG. 1 is provided in the measurement head described above. In FIG. 1, the configuration for performing alignment of the optical system with respect to the subject's eye is omitted from the figure.

The corneal endothelial cell imaging apparatus 1 includes an irradiation system 10 and a light receiving system 20. The irradiation system 10 includes an optical system for irradiating slit-shaped illumination light (slit light) toward a cornea C of a subject's eye E. The light receiving system 20 includes an optical system for receiving reflection component(s) from a corneal endothelium among reflected light from the cornea C of the subject's eye E irradiated with the illumination light by the irradiation system 10. The light receiving system 20 is arranged obliquely to the irradiation system 10 so that an optical axis O2 of the irradiation system 10 (for example, an optical axis of an objective lens in the irradiation system 10) intersects an optical axis O3 of the light receiving system 20 (for example, an optical axis of an objective lens in the light receiving system 20) at the cornea C. That is, when an axis in a front direction of the subject's eye E is O1, the irradiation system 10 is provided so that the angle between the axis O1 and the optical axis O2 of the irradiation system 10 is θi (e.g. θi=30 degrees), and the light receiving system 20 is provided so that the angle between the axis O1 and the optical axis O3 of the light receiving system 20 is θo. θo may be an angle equal to θi.

(Irradiation System 10)

The irradiation system 10 includes a light source 11, a slit 12 with a slit-shaped aperture, an optical scanner 13 as the spatial light modulator, lens systems L1 and L2, and an objective lens 15. The light source 11 includes, for example, an infrared LED (light emitting diode). On the slit 12, light from the light source 11 is irradiated. From the aperture formed in the slit 12, the slit-shaped illumination light is emitted as a secondary light source. The optical scanner 13 deflects the slit-shaped illumination light passing through the aperture formed in the slit 12 to guide the slit-shaped illumination light to the objective lens 15.

The optical scanner 13 changes the deflection angle of the illumination light from the slit 12, under the control from a controller described below. In FIG. 1, the optical scanner 13 is a one-axis scanner that one-dimensionally deflects the illumination light in a direction orthogonal to a slit direction (longitudinal direction of the slit).

In some embodiments, the optical scanner 13 two-dimensionally deflects the illumination light. In this case, the optical scanner 13 includes a first galvano scanner and a second galvano scanner. The first galvano scanner deflects the illumination light so as to move the illumination region of the illumination light in the slit direction (or a horizontal direction orthogonal to the optical axis of the irradiation system 10). The second galvano scanner deflects the illuminating light deflected by the first galvano scanner so as to move the illumination region of the illumination light in a direction orthogonal to the slit direction (or a vertical direction orthogonal to the optical axis of the irradiation system 10). Examples of scan mode for moving the illumination region of the illumination light using the optical scanner 13 include a horizontal scan, a vertical scan, a cross scan, a radial scan, a circle scan, a concentric scan, and a helical (spiral) scan.

By changing the deflection angle of the illumination light using the optical scanner 13, the illumination region (illuminated position) of the illumination light on the cornea C of the subject's eye E can be changed. In some embodiments, the optical scanner 13 sequentially changes the illumination region so that parts of the illumination regions overlap.

The lens system L1 includes one or more lenses, and is arranged between the light source 11 and the slit 12. The lens system L1 functions as a condenser lens to focus the light from the light source 11.

The lens system L2 includes one or more lenses, and is arranged between the slit 12 and the optical scanner 13. The lens system L2 functions as a collimator lens to convert the illumination light passing through the aperture formed in the slit 12 into collimated light.

The slit 12 (specifically, aperture of the slit 12) can be arranged at a position substantially conjugate optically to the corneal endothelium of the subject's eye E. The optical scanner 13 (specifically, deflection surface) can be arranged at a position substantially conjugate optically to the light source 11. The light source 11 is arranged at a front focal position of the lens system L1. The slit 12 is arranged at a front focal position of the lens system L2.

Light emitted from the light source 11 is focused by the lens system L1 and is irradiated on the slit 12. The light from the light source 11, the light passing through the aperture formed in the slit 12, is converted into collimated light by the lens system L2 and is irradiated onto the deflection surface of the optical scanner 13. The optical scanner 13 deflects the illumination light transmitted through the lens system L2 by changing the deflection angle of the deflection surface under the control from the controller described below, and guides the illumination light to the objective lens 15. The light having guided to the objective lens 15 is irradiated obliquely to the cornea C. By changing the deflection angle of deflection surface of the optical scanner 13, the illumination region of the slit-shaped illumination light on the cornea C can be changed.

(Light Receiving System 20)

The light receiving system 20 includes an objective lens 21, a plano-convex lens 22, a concave lens 23, a diaphragm 24 in that an aperture (slit) is formed, an imaging lens 25, and an image sensor 26. The objective lens 21, the plano-convex lens 22, and the imaging lens 25 are lenses with positive refractive power (positive lenses). The concave lens 23 is arranged between the objective lens 21 and the image sensor 26, and is a lens with negative refractive power (negative lens).

An optical center of the concave lens 23 is disposed at a position deviated from the optical axis of at least one of the objective lens 21 and the plano-convex lens 22, and the optical axis of the concave lens 23 is disposed so as to be inclined with respect to the optical axis of at least one of the objective lens 21 and the plano-convex lens 22 (tilt shift arrangement). At least one of the objective lens 21 and the plano-convex lens 22 may be tilt-shift arranged. That is, the optical center of the objective lens 21 may be disposed at a position deviated from the optical axis of the plano-convex lens 22, and the optical axis of the objective lens 21 may be arranged so as to be inclined with respect to the optical axis of the plano-convex lens 22.

The diaphragm 24 is disposed so that a portion of the reflected light flux from the corneal epithelium is shielded when the alignment of the optical systems (irradiation system 10 and the light receiving system 20) to the subject's eye E is matched and a portion of the reflected light flux from the corneal endothelium alone passes through the slit. The imaging lens 25 forms an image of the light passing through the concave lens 23 onto the light receiving surface of the image sensor 26. The image sensor 26 is a complementary metal oxide semiconductor (CMOS) image sensor. In some embodiments, the image sensor 26 is a charge coupled device (CCD) image sensor.

By increasing the imaging magnification using the imaging lens 25, the size of the light receiving surface of the image sensor 26 can be increased.

The diaphragm 24 is arranged so that the position of the aperture on an optical path of the reflected light from the cornea C is substantially conjugate optically to the corneal endothelium (cornea) of the subject's eye E. The light receiving surface (imaging surface, detection surface) of the image sensor 26 is arranged so that the position is substantially conjugate optically to the corneal endothelium (cornea) of the subject's eye E.

In some embodiments, the diaphragm 24 is removed from the configuration shown in FIG. 1 and the light passing through the concave lens 23 is configured to reach the imaging lens 25 directly.

Figure 2:
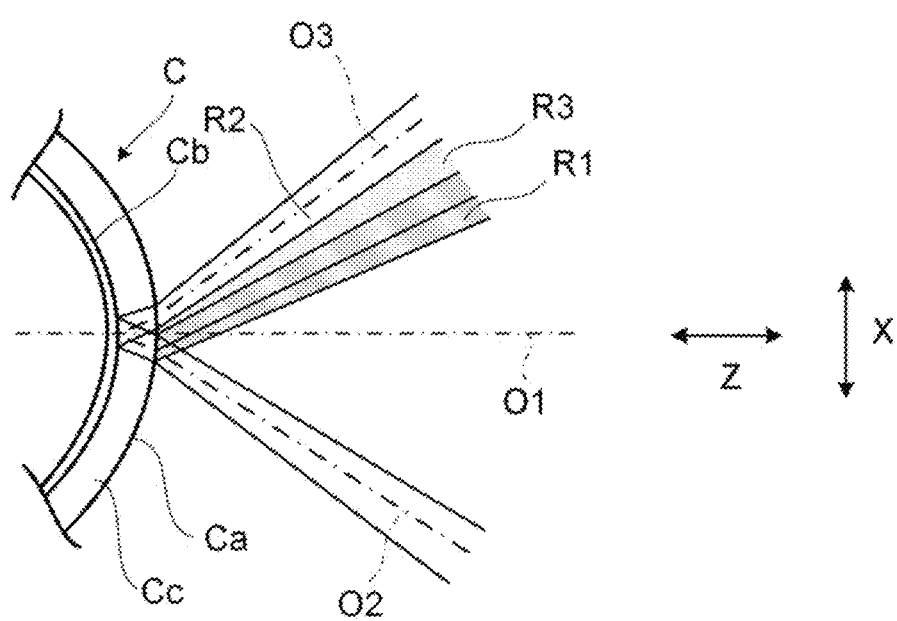
FIG. 2 is a diagram describing an operation of the corneal endothelial cell imaging apparatus according to the embodiments.

FIG. 2 shows a diagram describing the reflected light of the illumination light according to the embodiments. In FIG. 2, like reference numerals designate like parts as in FIG. 1. The same description may not be repeated.

The reflected light of the slit-shaped illumination light irradiated onto the cornea C by the irradiation system 10 is guided to the objective lens 21. The luminous flux of the reflected light includes the reflected luminous fluxes R1, R2, and R3, as shown in FIG. 2. The reflected luminous flux R1 is a reflected luminous flux of a corneal surface Ca. The corneal surface Ca is the corneal epithelium of the cornea C. The reflected luminous flux R2 is a reflected luminous flux of the corneal endothelium Cb. The reflected luminous flux R3 is a reflected luminous flux of a corneal stroma Cc of the cornea C. The reflected luminous fluxes R1, R2, and R3 pass through the objective lens 21, and pass through the plano-convex lens 22. The plano-convex lens 22 is tilt-shift arranged so as to correct the aberration characteristics of the light passing through it. Thereby, the aberration characteristics of the reflected luminous fluxes R1, R2, and R3 are corrected. The light passing through the plano-convex lens 22 is refracted by the concave lens 23.

Figure 3:
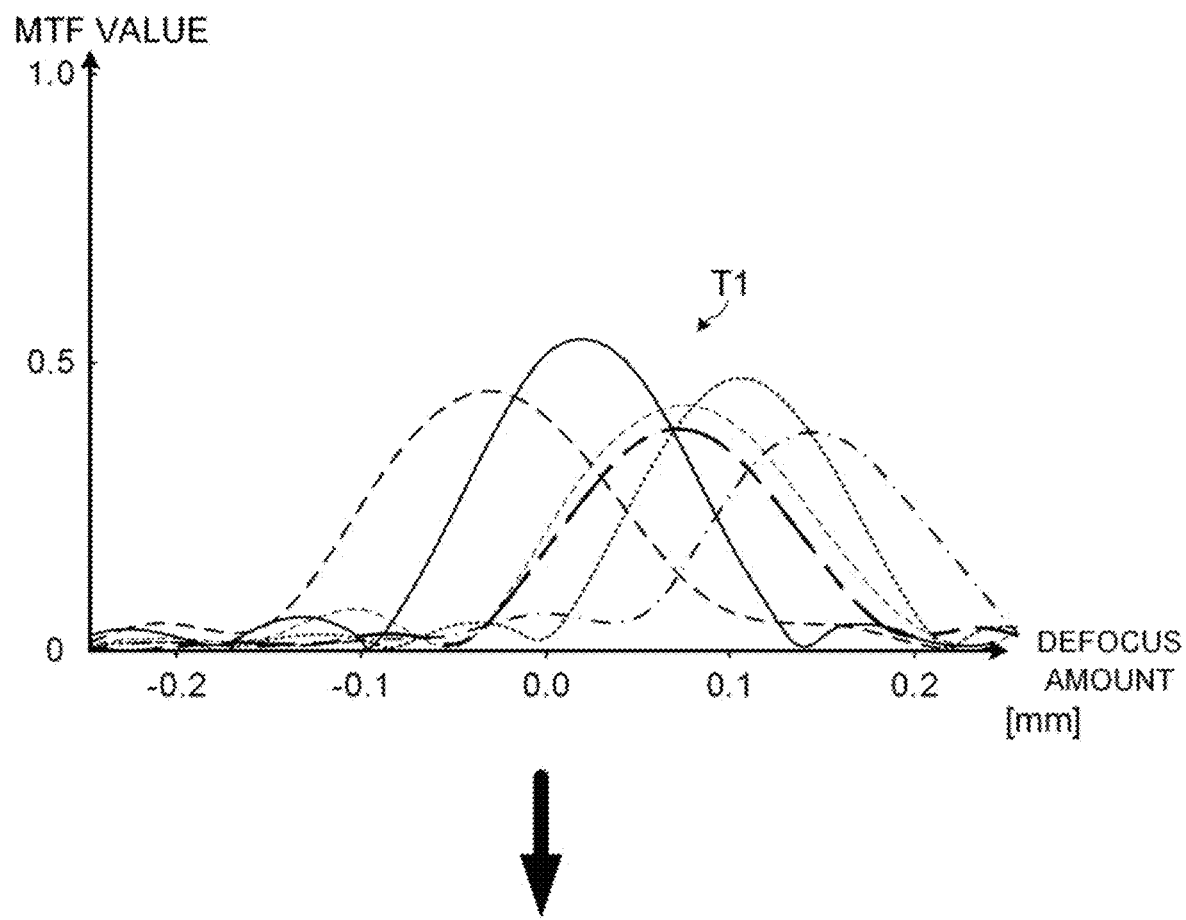
FIG. 3 is a diagram describing an operation of the corneal endothelial cell imaging apparatus according to the embodiments.
Figure 3:
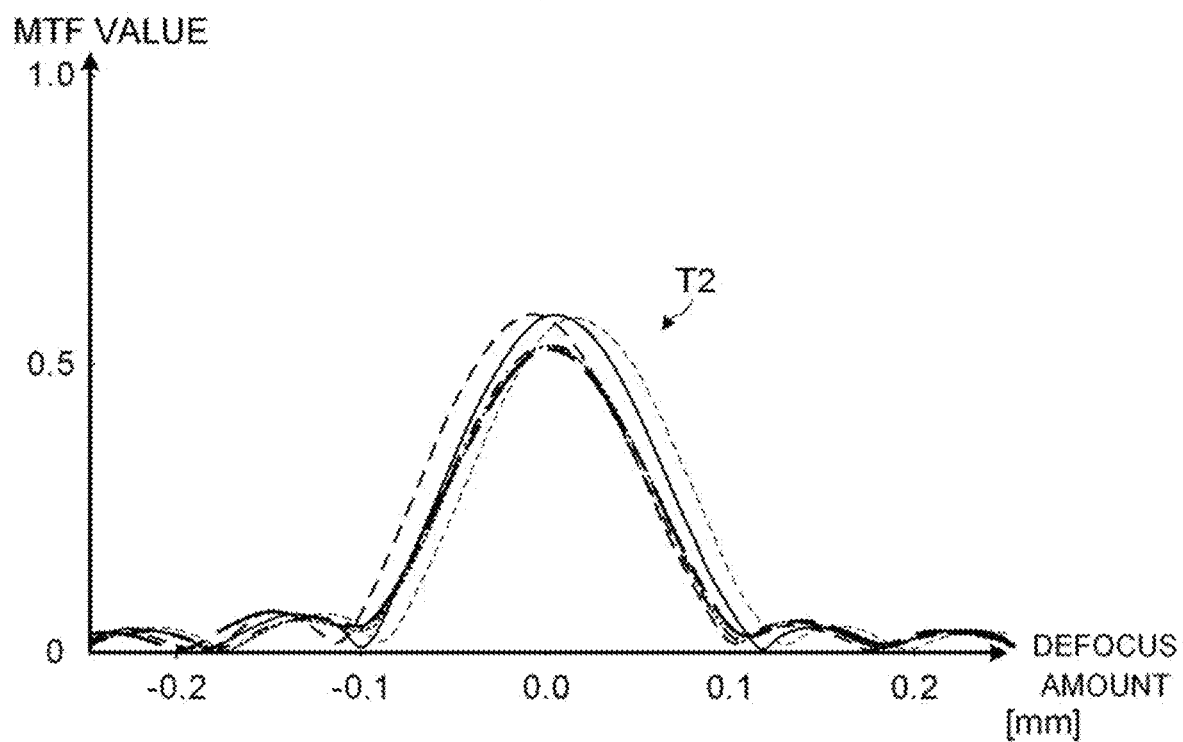

FIG. 3 schematically shows the change in imaging characteristics caused by the concave lens 23. In FIG. 3, the vertical axis represents the MTF (Modulation Transfer Function) value, and the horizontal axis represents the defocus amount. FIG. 3 schematically represents the MTF characteristics of the light passing through the optical center of the concave lens 23 (one point) and the positions near the four corners (four points) with reference to the optical center.

The characteristics T1 corresponds to the imaging characteristics caused by the concave lens 23 when the concave lens 23 is disposed coaxially with the optical axis O3 and the main surface is orthogonal to the optical axis O3. The characteristics T2 corresponds to the imaging characteristics caused by the concave lens 23 in the tilt shift arrangement as described above. Each of the optical center and the optical axis of the concave lens 23 is arranged as described above. Thereby, the imaging characteristics can be changed from the characteristic T1 to the characteristic T2. Comparing the characteristics T1 and T2, the tilt-shift arrangement can align the imaging characteristics of the passing light, in the lens plane of the concave lens 23. This allows to greatly reduce the focus difference between the corneal apex and its periphery. Therefore, even if the cornea is a conical cornea, etc., clear images of the corneal endothelial cells can be acquired with high resolution, independent of the morphology of the cornea.

In FIG. 1, the reflected luminous fluxes R1, R2, and R3 refracted by the concave lens 23 are irradiated on the diaphragm 24. Among the reflected luminous fluxes R1, R2, and R3 irradiated on the diaphragm 24, mainly the reflected luminous flux R2 passes through the slit and is imaged on the light receiving surface of the image sensor 26 by the imaging lens 25. As a result, the image of the corneal endothelial cell(s) is formed on the light receiving surface of the image sensor 26, and this image of the corneal endothelial cell(s) is captured.

The image sensor 26 is controlled by the controller described below, and the opening range is set so as to include the illumination range on the light receiving surface corresponding to the illumination region of the illumination light on the cornea C. Further, the image sensor 26 is controlled by the controller described below, and the light receiving result of the reflection components from the corneal endothelium obtained by the light receiving elements in the set opening range is read out from the image sensor 26. In particular, in case that the illumination region of the illumination light on the cornea C is sequentially moved through the deflection operation of the optical scanner 13, in the image sensor 26, the opening range in the light receiving surface corresponding to the illumination region on the cornea C is set sequentially. Further, the image sensor 26 is controlled so that the light receiving results of the reflection components from the corneal endothelium obtained by the light receiving elements in the set opening range are sequentially read out using rolling shutter method.

Figure 4:
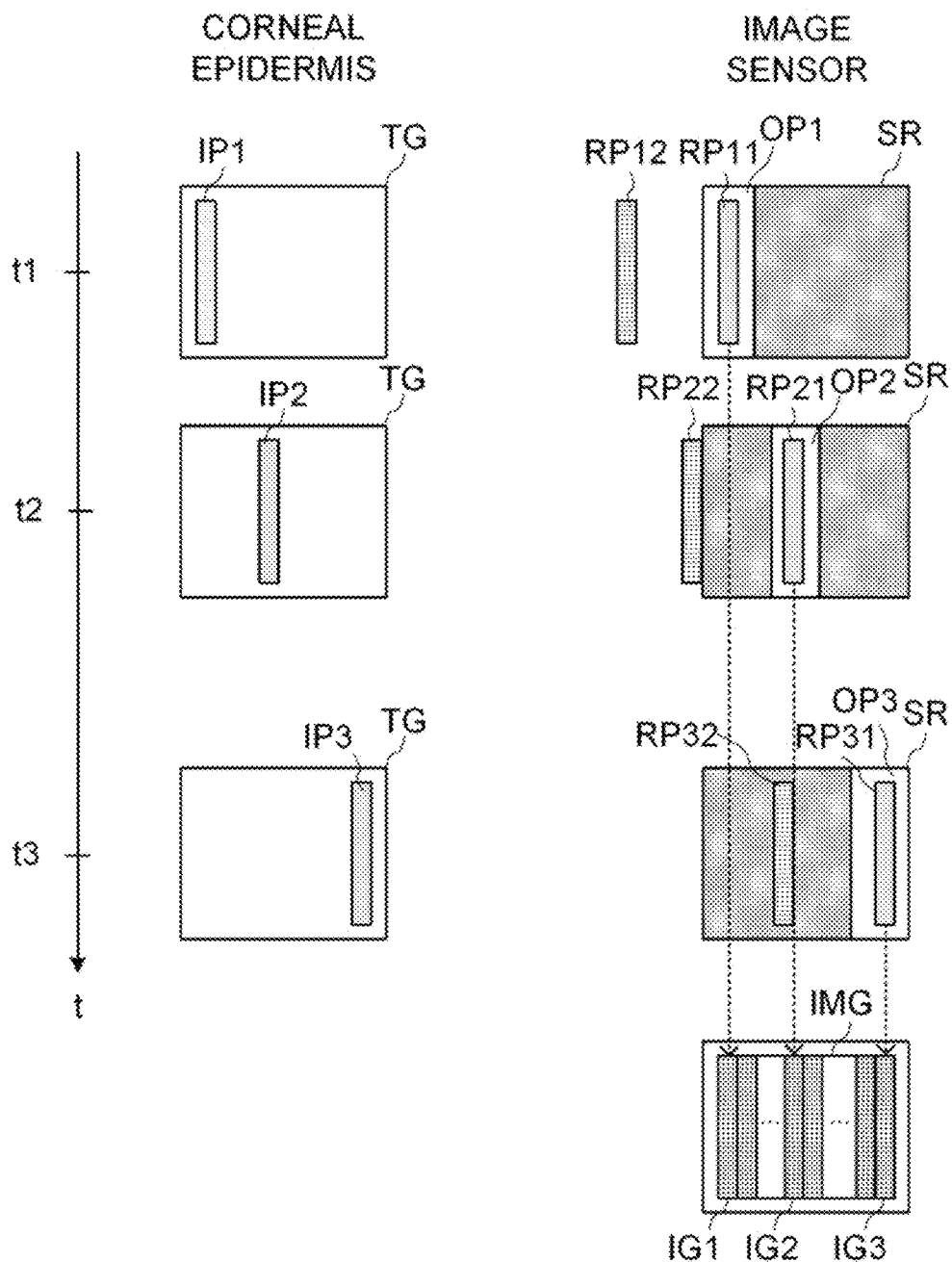
FIG. 4 is a diagram describing an operation of the corneal endothelial cell imaging apparatus according to the embodiments.

FIG. 4 shows a diagram describing content of the control for the image sensor 26. In FIG. 4, the vertical axis represents the time axis, and the illumination region of the illumination light on the corneal epidermis (corneal epithelium) at each time is schematically illustrated. Further, in FIG. 4, corresponding to the illumination region of the illumination light on the corneal epidermis, the illumination region (light receiving pattern) of the reflection component(s) from the corneal epithelium and the illumination region of the reflection component(s) from the corneal endothelium on the light receiving surface of the image sensor 26 at each time are illustrated schematically.

The slit-shaped illumination light is sequentially irradiated onto two or more illumination regions on the corneal epidermis TG of the cornea C through the deflection operation of the optical scanner 13. At time t1, the slit-shaped illumination light is irradiated onto the illumination region IP1 on the corneal epidermis TG. At time t2, the slit-shaped illumination light is irradiated onto the illumination region IP2 on the corneal epidermis TG. At time t3, the slit-shaped illumination light is irradiated onto the illumination region IP3 on the corneal epidermis TG.

When the corneal epidermis TG is irradiated with the illumination light, as shown in FIG. 2, the reflected light including the reflection components of each layer in the cornea C is guided to the light receiving system 20. For example, according to the configuration shown in FIG. 1, using the diaphragm 24, most of the components other than the reflected component(s) from the corneal endothelium can be shielded. In contrast, when the diaphragm 24 is removed, or even if the diaphragm 24 is provided, the light receiving surface SR of the image sensor 26 is irradiated with the reflection component(s) from the corneal epithelium and the reflection component(s) from the corneal endothelium at a predetermined interval in the direction orthogonal to the slit direction, as shown in FIG. 4.

The controller described below can set the opening range so as to include the illumination range of the reflected light (in particular, the reflection component(s) from the corneal endothelium) on the light receiving surface SR corresponding to the illumination region of the illumination light on the cornea C (corneal epidermis TG). The controller controls the image sensor 26 so as to read out the light receiving results of the light receiving result(s) obtained by the light receiving elements in the set opening range, for example, using rolling shutter method.

At time t1, when the illumination region IP1 on the corneal epidermis TG is irradiated with the illumination light, the opening range OP1 on the light receiving surface SR corresponding to the illumination region IP1 is set in the image sensor 26. The opening range OP1 includes an illumination range RP11 of the reflection component(s) from the corneal endothelium on the light receiving surface SR corresponding to the illumination region IP1. At time t1, the illumination range RP12 of the reflection component(s) from the corneal epithelium on the light receiving surface SR is not included in the opening range OP1.

In the same way, at time t2, when the illumination region IP2 on the corneal epidermis TG is irradiated with the illumination light, the opening range OP2 on the light receiving surface SR corresponding to the illumination region IP2 is set in the image sensor 26. The opening range OP2 includes an illumination range RP21 of the reflection component(s) from the corneal endothelium on the light receiving surface SR corresponding to the illumination region IP2. At time t2, the illumination range RP22 of the reflection component(s) from the corneal epithelium on the light receiving surface SR is not included in the opening range OP2.

Further, at time t3, when the illumination region IP3 on the corneal epidermis TG is irradiated with the illumination light, the opening range OP3 on the light receiving surface SR corresponding to the illumination region IP3 is set in the image sensor 26. The opening range OP3 includes an illumination range RP31 of the reflection component(s) from the corneal endothelium on the light receiving surface SR corresponding to the illumination region IP3. At time t3, the illumination range RP32 of the reflection component(s) from the corneal epithelium on the light receiving surface SR is not included in the opening range OP3.

This easily allows to efficiently receive the light receiving result alone corresponding to the reflection component(s) from the corneal endothelium, without being affected by the reflected light (unnecessary light) irradiated onto other than the opening range.

For example, as shown in FIG. 4, by synthesizing images IG1, IG2, IG3, etc. formed from the light receiving results acquired by the light receiving elements in the opening range at each time based on the positions of the opening ranges, a high quality panoramic image IMG with a wide field of view of the corneal endothelial cells can be acquired.

[Control System]

Figure 5:
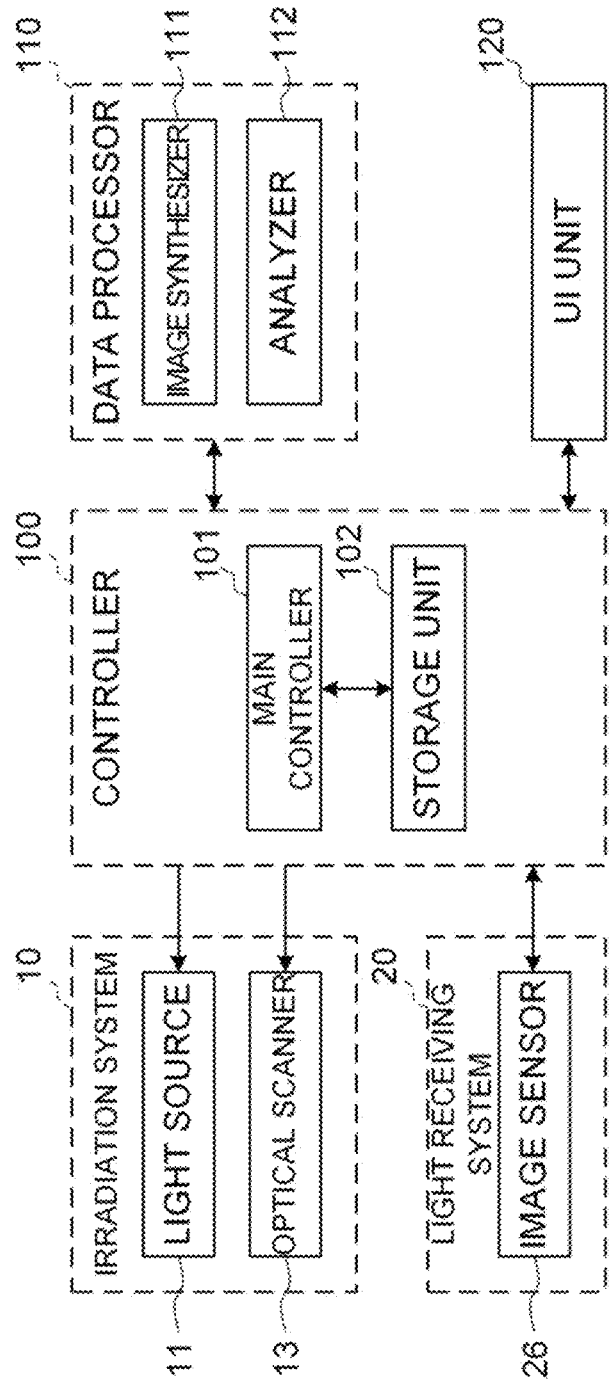
FIG. 5 is a schematic diagram illustrating an example of a configuration of a control system of the corneal endothelial cell imaging apparatus according to the embodiments.

FIG. 5 shows a block diagram of an example of a control system of the corneal endothelial cell imaging apparatus 1. The control system of the corneal endothelial cell imaging apparatus 1 is configured with the controller 100 as the center.

(Controller 100)

The controller 100 controls each part of the corneal endothelial cell imaging apparatus 1. The controller 100 includes a main controller 101 and a storage unit 102. The functions of the main controller 101 are realized by a processor, for example.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

The storage unit 102 stores, in advance, computer programs for controlling the corneal endothelial cell imaging apparatus 1. The computer programs include a program for controlling the light source, a program for controlling the image sensor, a program for data processing, and a program for user interface, and the like. The main controller 101 operates according to the computer programs, and thereby the controller 100 performs the control process.

Examples of the control for the irradiation system 10 include control for the light source 11 and a control for the optical scanner 13. Examples of the control for the light source 11 include switching the light source 11 on and off, adjustment of light amount. Examples of the control for the optical scanner 13 include control of the deflection start position, the deflection end position, the deflection angle range, and the deflection speed.

Examples of the light receiving system 20 include control for the image sensor 26. Examples of the control for the image sensor 26 include setting of the opening range on the light receiving surface, read out control of the light receiving results, adjustment of exposure, adjustment of gain, adjustment of imaging rate. For example, the controller 100 sets the opening range on the light receiving surface for the image sensor 26 in accordance with the position of the illumination region of the illumination light on the corneal epidermis. Further, the controller 100 controls the image sensor 26 so as to read out the light receiving results obtained by the light receiving elements in the set opening range using rolling shutter method. The controller 100 can acquire output signal(s) (video signal(s)) from the image sensor 26 by reading out the light receiving results obtained by the light receiving elements in the opening range.

The controller 100 controls the display device included in the UI unit 120 described below to display various kinds of information. Examples of the information displayed on the display device include information generated by the controller 100 and information after data processing performed by the data processor 110. Further, the controller 100 can control each part of the corneal endothelial cell imaging apparatus 1 based on operation content for the UI unit 120 described below.

(Data Processor 110)

The data processor 110 executes various kind of data processing. Examples of the data processing include processing on the light receiving results (image data) obtained by the image sensor 26. Examples of the processing include various types of image processing, analytical processing on images, and diagnosis support processing such as image evaluation based on the image data.

The data processor 110 includes an image synthesizer 111 and an analyzer 112.

The image synthesizer 111 generates a synthetic image (panoramic image) by synthesizing two or more images. The two or more images are obtained by illuminating illumination regions different from each other on the cornea C (corneal epidermis) with the slit-shaped illumination light through the deflection operation of the optical scanner 13. In some embodiments, the image synthesizer 111 performs position matching processing on two images, the two images being obtained so that portions of the edges of the images overlap each other by irradiating the illumination light so that the edges of adjacent illumination regions overlap, so that the overlapping portions match. The image synthesizer 111 synthesizes the two images by arranging the two images, on which the position matching processing is performed, side by side. The image synthesizer 111 generates the synthetic image by repeating such a synthetic processing.

The analyzer 112 obtains information representing a state of the corneal endothelial cell(s) based on the output signal(s) from the image sensor 26. For example, the analyzer 112 specifies boundaries of the corneal endothelial cells by analyzing the image, in which a plurality of corneal endothelial cells is depicted, generated based on the output signal(s) from the image sensor 26, and specifies the corneal endothelial cells based on the specified boundaries. In some embodiments, the analyzer 112 specifies the corneal endothelial cells by analyzing the synthetic image generated by the image synthesizer 111. The analyzer 112 obtains the area of the specified corneal endothelial cell(s) or the shape of the specified corneal endothelial cell(s), and obtains the information representing the state of the corneal endothelial cell(s). Examples of the information representing the state of the corneal endothelial cell(s) include number of cells, density of cells, minimum cell area, maximum cell area, average cell area, standard deviation of cell area, coefficient of variation of cell area, histogram of cell area, hexagonal cell appearance rate, and histogram of shape.

In some embodiments, the analyzer 112 obtains the information representing the above state of the corneal endothelial cell(s) for the corneal endothelial cell(s) in a region to be analyzed in the image specified using the UI unit 120.

In some embodiments, the analyzer 112 specifies the corneal endothelial cell having the minimum cell area or the maximum cell area. The main controller 101 displays the corneal endothelial cell(s) specified by the analyzer 112 from the corneal endothelial cells depicted in the image on the display device so that the specified corneal endothelial cell(s) can be identified.

In some embodiments, the analyzer 112 specifies a region where the corneal endothelial cell(s), in which the above information representing the state of the corneal endothelial cell(s) satisfies a predetermined condition, is/are depicted. For example, the analyzer 112 specifies the region having greater than or equal to a predetermined density in the image, the region having less than a predetermined density in the image, or the region having a predetermined density range in the image. For example, the analyzer 112 specifies the region in which the corneal endothelial cells less than or equal to the average cell area are depicted in the image, the region in which the corneal endothelial cells greater than or equal to the average cell area are depicted in the image, or the region in which the corneal endothelial cells within a predetermined area range including the average cell area are depicted in the image. The main controller 101 displays the region specified by the analyzer 112 from the image, in which the plurality of corneal endothelial cells is depicted, so that the specified region can be identified.

It should be noted that the image synthesizer 111 may perform position matching of the two image based on the boundaries of the corneal endothelial cells in the overlap region specified by the analyzer 112, and may synthesize the two images by arranging the two image, on which the position matching has been performed, side by side.

The functions of the data processor 110 are implemented by one or more processors, for example. In some embodiments, the function of the image synthesizer 111 is realized by an image synthesis processor, and the function of the analyzer 112 is realized by an analysis processor.

(UI Unit 120)

The UI (user interface) unit 120 has a function for interchanging information between a user and the corneal endothelial cell imaging apparatus 1. The UI unit 120 includes a display device and an operation device (input device). The display device may include a display unit, and it may include another display device. The operation device includes various hardware keys and/or software keys. Upon receiving the operation content for the operation device, the controller 100 can output a control signal corresponding to the operation content to each part. At least a part of the display device and at least a part of the operation device may be configured integrally. One example of this is the touch panel display.

The lens system L1 is an example of the "first lens system" according to the embodiments. The lens system L2 is an example of the "second lens system" according to the embodiments.

[Operation]

The operation of the corneal endothelial cell imaging apparatus 1 according to the embodiments will be described.

Figure 6:
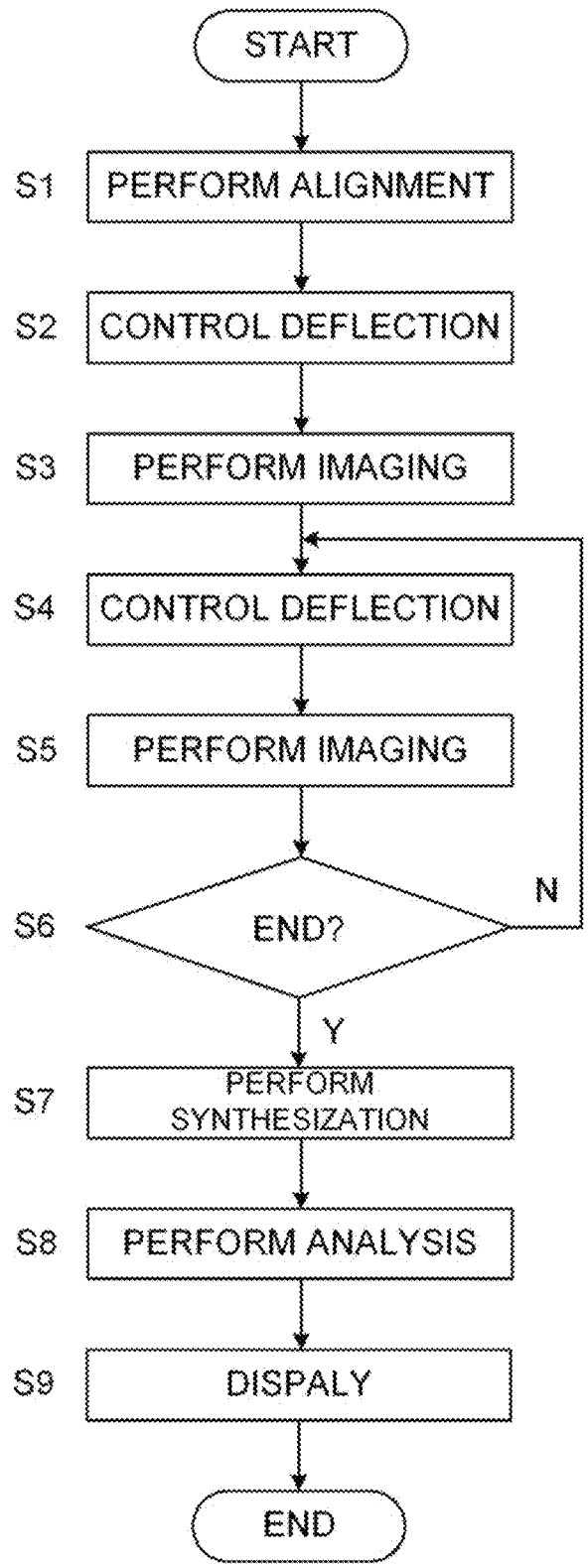
FIG. 6 is a flow chart of an example of an operation of the corneal endothelial cell imaging apparatus according to the embodiments.

FIG. 6 shows an example of an operation of the corneal endothelial cell imaging apparatus 1 according to the embodiments. FIG. 6 represents the flow chart of an example of the operation of the corneal endothelial cell imaging apparatus 1 according to the embodiments in case of acquiring the panoramic image of the corneal endothelial cells. The storage unit 102 stores a computer program for realizing the processing shown in FIG. 6. The main controller 101 operates according to the computer program, and thereby the main controller 101 performs the processing shown in FIG. 6.

(S1: Perform Alignment)

The main controller 101 performs position matching of the optical system in the XY direction with respect to the subject's eye E, using a known alignment method.

For example, the main controller 101 projects alignment visual target light onto the subject's eye E using an alignment visual target projection system (not shown), and forms an image of reflected light of the alignment visual target light on the light receiving surface of the image sensor 26. Thereby, the image caused by the Purkinje image of the XY alignment visual target light is formed on the light receiving surface. The main controller 101 displays the image caused by the alignment visual target light on the display device of the UI unit 120 based on the light receiving result of the reflected light of the alignment visual target light obtained by the image sensor 26. The user moves the measurement head including the optical system in the XY direction to perform XY alignment, by operating on the operation device included in the UI unit 120 so as to guide the image within a predetermined alignment mark. In case of automatic alignment, the main controller 101 moves the measurement head in the XY direction so as to cancel displacement of the image with reference to the alignment mark.

Next, the main controller 101 performs position matching of the optical system in the Z direction with respect to the subject's eye E, using a known alignment method. For example, the main controller 101 projects light for performing Z alignment from an oblique direction using a Z alignment visual target projection system (not shown). The light may be the slit-shaped light. The main controller 101 receives reflected light of the light with a line sensor (not shown), etc. and moves the measurement head including the optical system to perform Z alignment so that a received position of the reflected light is a position determined in advance as a position where the alignment in the Z direction is appropriate.

(S2: Control Deflection)

Subsequently, the main controller 101 starts the deflection operation of the optical scanner 13 within a predetermined deflection operation range. In step S2, the main controller 101 deflects the deflection surface of the optical scanner 13 by a predetermined deflection angle with reference to a deflection start angle. Thereby, the slit-shaped illumination light is irradiated onto a predetermined illumination region on the cornea C. Step S2 corresponds to the "irradiation system control step" according to the embodiments.

(S3: Perform Imaging)

In synchronization with the deflection control in step S2, the main controller 101 sets the opening rage for the image sensor 26 so as to include the illumination range on the light receiving surface SR corresponding to the illumination region on the cornea C set in step S2. Subsequently, the main controller 101 controls the image sensor 26 to acquire the light receiving results obtained by the light receiving elements in the set opening range. Step S3 corresponds to the "light receiving system control step" according to the embodiments.

The main controller 101 acquires the light receiving results obtained by the image sensor 26, and stores the image data (or video signals) based on the light receiving results in the storage unit 102.

(S4: Control Deflection)

Subsequently, the main controller 101 deflects the deflection surface of the optical scanner 13 by a predetermined deflection angle. Thereby, the illumination region on the cornea C moves in the direction orthogonal to the slit direction, and the slit-shaped illumination light is irradiated onto the moved illumination region. Step S4 corresponds to the "irradiation system control step" according to the embodiments, in the same way as step S2.

For example, in step S4, the illumination region after moving is set so as to overlap a part of the illumination region set in step S2.

(S5: Perform Imaging)

In the same way as step S3, in synchronization with the deflection control in step S4, the main controller 101 sets the opening rage for the image sensor 26 so as to include the illumination range on the light receiving surface SR corresponding to the illumination region on the cornea C set in step S4. Further, the main controller 101 controls the image sensor 26 to acquire the light receiving results obtained by the light receiving elements in the set opening range. Step S5 corresponds to the "light receiving system control step" according to the embodiments, in the same way as step S3.

The main controller 101 acquires the light receiving results obtained by the image sensor 26, and stores the image data (or video signals) based on the light receiving results in the storage unit 102.

(S6: END?)

Next, main controller 101 determines whether or not to terminate the imaging. The number of times to perform imaging while changing the irradiation region of the cornea C is determined in advance. The main controller 101 can determine whether or not to terminate the imaging based on the number of times. Further, the main controller 101 may determine whether or not to perform the next imaging based on the operation content for the operation device in the UI unit 120.

When it is determined that the imaging is to be terminated (S6: Y), the operation of the corneal endothelial cell imaging apparatus 1 proceeds to step S7. When it is determine that the photographing is not to be terminated (S6: N), the operation of the corneal endothelial cell imaging apparatus 1 proceeds to step S4.

(S7: Perform Synthesization)

When it is determined that the imaging is to be terminated in step S6 (S6: Y), the main controller 101 controls the image synthesizer 111 to generate the synthetic image of the two or more images acquired in step S3 and in repeated step S5. Step S7 corresponds to the "image synthesizing step" according to the embodiments.

(S8: Perform Analysis)

Next, the analyzer 112 obtains the information representing the state of the corneal endothelial cells by analyzing the synthetic image generated in step S7. Step S8 corresponds to the "analyzing step" according to the embodiments.

(S9: Display)

Next, the main controller 101 displays the information obtained in step S8 on the display device of the UI unit 120. In this case, the main controller 101 can display the information on the display device along with the synthetic image generated in step S7. In some embodiments, the main controller 101 displays the information obtained in step S8 on the display device so that the information is superimposed on the synthetic image generated in step S7.

This terminates the operation of the corneal endothelial cell imaging apparatus 1 (END).

As described above, the irradiation system 10 irradiates the illumination light so that the illumination region on the cornea C moves in the direction orthogonal to the slit direction by deflecting the slit-shaped illumination light using the optical scanner 13. The light receiving system 20 sets the opening range on the light receiving surface corresponding to the illumination region on the cornea C in synchronization with the movement of the illumination region, and captures the light receiving results obtained by the light receiving elements in the set opening range using rolling shutter method.

This allows to speed up the sequential irradiation of the slit-shaped illumination light onto the different illumination regions on the corneal endothelium. In addition, by moving the opening range on the light receiving surface in synchronization with the movement of the illumination region of the illumination light on the cornea, this allows to efficiently receive the reflection component(s) from the corneal endothelium without being affected by unnecessary reflection component(s) (e.g., the reflection component(s) from the corneal epithelium). Further, the images of the corneal endothelial cells necessary for generating the panoramic image can be acquired in a short time with a highly simple configuration.

For example, the time required to acquire an image in which new corneal endothelial cells are depicted by changing the presentation position of the fixation target is at least 10 to 20 seconds, and the eye moves during this time. In this case, the eye movement makes it difficult to perform position matching of the images and often prevents the panoramic images from being generated. In contrast, in the embodiments, the time required to acquire a new image can be greatly reduced. Thereby, this enables to acquire panoramic images easily without placing a burden on the subject.

Further, the light receiving system 20 is configured to provide the concave lens 23 between the objective lens 21 and the image sensor 26, and the concave lens 23 is tilt-shift arranged. This allows to greatly reduce the focus difference between the corneal apex and its periphery. Therefore, even if the cornea is a conical cornea, etc., clear images of the corneal endothelial cells can be acquired with high resolution, independent of the morphology of the cornea. In addition, the focus difference at any two positions in the acquired image of corneal endothelial cells is small. Thereby, it becomes easier to perform position matching of these images, and it becomes easier to acquire panoramic images.

Modification Example

The configuration of the optical system of the corneal endothelial cell imaging apparatus 1 according to the embodiments is not limited to the configuration shown in FIG. 1.

Figure 7:
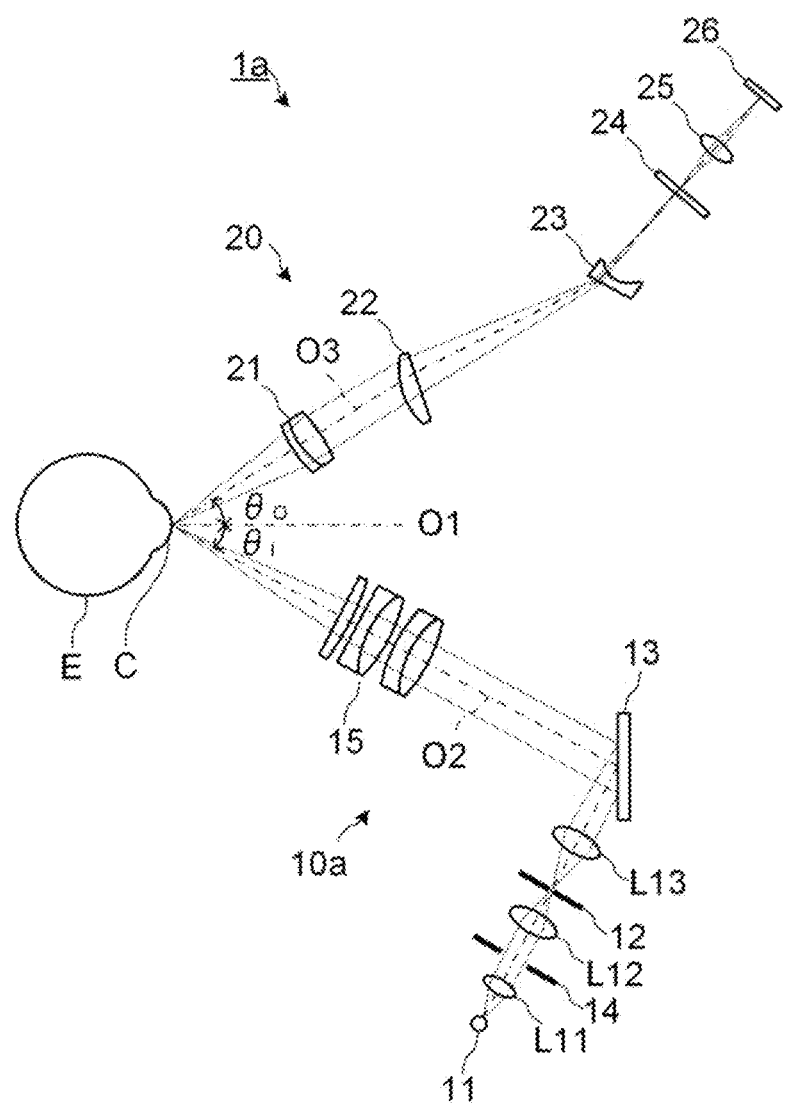
FIG. 7 is a schematic diagram illustrating an example of a configuration of an optical system of a corneal endothelial cell imaging apparatus according to a modification example of the embodiments.

FIG. 7 shows an example of a configuration of an optical system of a corneal endothelial cell imaging apparatus according to a modification example of the embodiments. FIG. 7 represents the example of the configuration of the optical system in case of performing Kohler illumination on the corneal endothelial cells. In FIG. 7, parts similarly configured to those in FIG. 1 are denoted by the same reference numerals, and the description thereof is omitted unless it is necessary.

The configuration of the corneal endothelial cell imaging apparatus 1a according to the present modification example differs from that of the corneal endothelial cell imaging apparatus 1 in that an irradiation system 10a is provided in place of the irradiation system 10.

The irradiation system 10a includes the light source 11, the slit 12, the optical scanner 13, lens systems L11, L12, and L13, the diaphragm (field diaphragm) 14, and the objective lens 15. Between the light source 11 and the optical scanner 13, the lens system L11, the diaphragm 14, the lens system L12, the slit 12, and the lens system L13 are arranged in order from the light source 11 side.

The lens system L11 includes one or more lenses, and is arranged between the light source 11 and the diaphragm 14. The light source 11 is arranged at a front focal position of the lens system L11. The lens system L11 functions as a condenser lens to focus the light from the light source 11.

In the diaphragm 14, an apertures is formed. In some embodiments, the size of the aperture formed in the diaphragm 14 can be changed. The light from the light source 11, the light passing through the lens system L11, passes through the aperture formed in the diaphragm 14, and is irradiated onto the lens system L12.

The lens system L12 includes one or more lenses, and is arranged between the diaphragm 14 and the slit 12. The lens system L12 functions as a relay lens.

The light source 11 is arranged at a position substantially conjugate optically to the slit 12 (specifically the aperture of the slit 12). The diaphragm 14 is arranged at a position substantially conjugate optically to the corneal endothelium. The slit 12 (specifically, aperture of the slit 12) is arranged at a position substantially conjugate optically to the corneal endothelium of the subject's eye E.

The lens system L13 includes one or more lenses, and is arranged between the slit 12 and the optical scanner 13. The lens system L13 functions as a collimator lens to convert the illumination light passing through the aperture formed in the slit 12 into collimated light. The slit 12 is arranged at a front focal position of the lens system L13.

In the present modification example, the light source 11 is arranged at a position non-conjugate to the optical scanner 13.

Light emitted from the light source 11 is focused by the lens system L11 and passes through the aperture formed in the diaphragm 14, is transmitted through the lens system L12, and is irradiated onto the slit 12. The light from the light source 11, the light passing through the aperture formed in the slit 12, is converted into collimated light by the lens system L13, and is irradiated onto the deflection surface of the optical scanner 13. The optical scanner 13 deflects the illumination light transmitted through the lens system L13 by changing the deflection angle of the deflection surface under the control from the controller, and guides the illumination light to the objective lens 15. The light having guided to the objective lens 15 is irradiated obliquely to the cornea C. By changing the deflection angle of deflection surface of the optical scanner 13, the illumination region of the slit-shaped illumination light on the cornea C can be changed.

The operation of the corneal endothelial cell imaging apparatus 1a according to the present modification example is similar to the operation of the corneal endothelial cell imaging apparatus 1 according to the embodiments. Therefore, the detailed description thereof will be omitted.

As described above, according to the present modification example, the image of the light source 11 is formed at the aperture of the slit 12, and the image of the diaphragm 14 is formed on the corneal endothelium. Thereby, the same effect as in the embodiments can be obtained while uniformly illuminating the cornea.

In the embodiments described above or the modification example thereof, a case where the illumination light is irradiated onto the illumination region with a fixed size (area) for the cornea C is described. However, the configuration according to the embodiments is not limited to this. For example, the size of the aperture formed in the slit 12 or the shape of the aperture formed in the slit 12 may be able to be changed. In case that a predetermined imaging region on the cornea C is covered with a plurality of illumination regions through the deflection operation of the optical scanner 13, by changing the size of the aperture formed in the slit 12 or the shape of the aperture formed in the slit 12 during the acquisition of a series of images, the size of at least one of the plurality of illumination regions described above is changed. When the reflection components from the corneal endothelium in the illumination region whose size has been changed are received, the size of the opening range on the light receiving surface corresponding to the illumination region whose size has been changed is also changed. Thereby, the image of the corneal endothelial cells in the imaging region with a desired size or a desired shape can be acquired.

In the embodiments described above or the modification example thereof, one of the images of the corneal endothelial cells shown in FIG. 4 can be reacquired. In this case, the deflection angles of the optical scanner 13 corresponding to each of a plurality of illumination regions of the illumination light irradiated on the cornea C are stored in the storage unit 102. The main controller 101 reads out the deflection angle of the optical scanner 13 corresponding to a desired illumination region, and deflects the deflection surface of the optical scanner 13 to the deflection angle read out. Further, the main controller 101 sets the opening range on the light receiving surface corresponding to the desired illumination region for the image sensor 26. This makes it possible to reacquire images of the corneal endothelial cells in the desired imaging region by performing re-imaging with the desired illumination region illuminated. In some embodiments, the image synthesizer 111 generates the synthetic image from a plurality of images of the corneal endothelial cells, the images including the reacquired image of the corneal endothelial cells.

In the embodiments described above or the modification example thereof, two or more slit-shaped apertures may be formed in the slit 12. In this case, two or more slit-shaped illumination light with different illumination regions each other are simultaneously irradiated on a predetermined imaging region on the cornea C. In this case, two or more opening ranges on the light receiving surface corresponding to each two or more illumination regions on the cornea C are simultaneously set, and the light receiving results obtained by the light receiving elements in the two or more opening ranges are sequentially read out, or are read out using rolling shutter method.

In the embodiments described above or the modification example thereof, a case where the illumination region of the slit-shaped illumination light is moved in the direction orthogonal to the slit direction is described. However, the configuration according to the embodiments is not limited to these. For example, the illumination region of the slit-shaped illumination light may be moved in the slit direction. For example, the synthetic image (panoramic image) including a first synthetic image and a second synthetic image can be formed. Here, the first synthetic image is acquired by synthesizing two images of the corneal endothelial cells adjacent to each other in the direction orthogonal to the slit direction. The second synthetic image is acquired by synthesizing two images of the corneal endothelial cells adjacent to each other in the slit direction.

[Actions]

Actions of the embodiments will be described.

A corneal endothelial cell imaging apparatus (1, 1a) according to some embodiments includes an irradiation system (10, 10a), a light receiving system (20), and a controller (100, main controller 101). The irradiation system includes a spatial light modulator (optical scanner 13) modulating light from a light source (11), and is configured to irradiate slit-shaped illumination light toward a cornea (C) of a subject's eye (E) by modulating the light from the light source using the spatial light modulator. The light receiving system is arranged obliquely to the irradiation system, and includes an image sensor (26) receiving reflected light from the cornea. The controller is configured to control the spatial light modulator so as to irradiate the illumination light onto an illumination region on the cornea, and is configured to control the image sensor to set an opening range on a light receiving surface corresponding to the illumination region on the cornea and to capture a light receiving result of reflection component from a corneal endothelium obtained by a light receiving element in the set opening range.

According to such an aspect, the spatial light modulator and the image sensor are controlled so as to synchronize the irradiation of the illumination light onto the desired illumination region on the cornea using the spatial light modulator and the setting of the opening range on the light receiving surface corresponding to the illumination region on the cornea. This allows to image the corneal endothelial cell(s) at high speed. Further, by capturing the light receiving result of the reflection component from the corneal endothelium obtained by the light receiving element in the set opening range, the reflection component from the corneal endothelium can be efficiently received with a simple configuration, without being affected by unnecessary reflection component (e.g., the reflection component from the corneal epithelium). Therefore, high quality images of the corneal endothelial cell can be acquired easily.

In the corneal endothelial cell imaging apparatus according to some embodiments, the controller is configured to control the spatial light modulator so as to sequentially irradiate the illumination light onto two or more illumination regions on the cornea, and is configured to control the image sensor to sequentially set two or more opening ranges on the light receiving surface corresponding to the illumination regions on the cornea and to sequentially capture the light receiving results of reflection component from the corneal endothelium obtained by the light receiving elements in the set opening range.

According to such an aspect, the opening range on the light receiving surface can be moved in synchronization with the movement of the illumination region of the illumination light on the cornea. Thereby, images of the corneal endothelial cell with a wide field of view can be acquired in a short time with a highly simple configuration.

The corneal endothelial cell imaging apparatus according to some embodiments further includes an image synthesizer (111) configured to generate a synthetic image by synthesizing two or more images based on the light receiving results obtained by the light receiving elements in the two or more opening ranges on the light receiving surface.

According to such an aspect, Thereby, images with a wide field of view (for example, panoramic image) can be easily acquired with a highly simple configuration, without placing a burden on the subject.

The corneal endothelial cell imaging apparatus according to some embodiments further includes an analyzer (112) configured to obtain information representing a state of corneal endothelial cells by analyzing the synthetic image.

According to such an aspect, highly accurate information on the corneal endothelial cell(s) can be easily provided.

In the corneal endothelial cell imaging apparatus according to some embodiments, the irradiation system includes a slit (12) in which an aperture is formed, the slit being configured to be irradiated by the light from the light source, and the spatial light modulator includes an optical scanner (13) configured to deflect the slit-shaped illumination light passing through the aperture formed in the slit.

According to such an aspect, the spatial light modulator and the image sensor are controlled so as to synchronize the irradiation of the illumination light onto the desired illumination region on the cornea through the deflection operation of the optical scanner and the setting of the opening range on the light receiving surface corresponding to the illumination region on the cornea. This allows to image the corneal endothelial cell(s) at high speed and to easily acquire high quality images of the corneal endothelial cell(s), with a highly simple configuration.

In the corneal endothelial cell imaging apparatus according to some embodiments, the slit is arranged at a position substantially conjugate optically to the corneal endothelium.

According to such an aspect, since the illumination light can be irradiated onto the cornea with sufficient illumination level, higher quality images of the corneal endothelial cell can be acquired.

In the corneal endothelial cell imaging apparatus according to some embodiments, the optical scanner is arranged at a position substantially conjugate optically to the light source.

According to such an aspect, since the illumination light can be irradiated onto the cornea with sufficient illumination level, higher quality images of the corneal endothelial cell can be acquired.

The corneal endothelial cell imaging apparatus according to some embodiments further includes a first relay lens system (lens system L1) arranged between the light source and the slit; and a second relay lens system (lens system L2) arranged between the slit and the optical scanner, wherein the light source is arranged at a front focal position of the first relay lens system, and the slit is arranged at a front focal position of the second relay lens system.

According to such an aspect, even if the size of the aperture formed in the slit is sufficiently small, highly efficient illumination onto the cornea can be performed.

A method of controlling a corneal endothelial cell imaging apparatus according to the embodiments is a method of controlling the corneal endothelial cell imaging apparatus (1, 1a) including an irradiation system (10, 10a), and a light receiving system (20). The irradiation system includes a spatial light modulator (optical scanner 13) modulating light from a light source (11), and configured to irradiate slit-shaped illumination light toward a cornea (C) of a subject's eye (E) by modulating the light from the light source using the spatial light modulator. The light receiving system is arranged obliquely to the irradiation system, and includes an image sensor (26) receiving reflected light from the cornea. The method of controlling the corneal endothelial cell imaging apparatus includes an irradiation system control step and a light receiving system control step. The irradiation system control step is performed to control the spatial light modulator so as to irradiate the illumination light onto an illumination region on the cornea. The light receiving system control step is performed to control the image sensor to set an opening range on a light receiving surface corresponding to the illumination region on the cornea and to capture a light receiving result of reflection component from a corneal endothelium obtained by a light receiving element in the set opening range.

According to such an aspect, the spatial light modulator and the image sensor are controlled so as to synchronize the irradiation of the illumination light onto the desired illumination region on the cornea using the spatial light modulator and the setting of the opening range on the light receiving surface corresponding to the illumination region on the cornea. This allows to image the corneal endothelial cell(s) at high speed. Further, by capturing the light receiving result of the reflection component from the corneal endothelium obtained by the light receiving element in the set opening range, the reflection component from the corneal endothelium can be efficiently received with a simple configuration, without being affected by unnecessary reflection component (e.g., the reflection component from the corneal epithelium). Therefore, high quality images of the corneal endothelial cell can be acquired easily.

In the method of controlling the corneal endothelial cell imaging apparatus according to some embodiments, the irradiation system control step is performed to control the spatial light modulator so as to sequentially irradiate the illumination light onto two or more illumination regions on the cornea, and the light receiving system control step is performed to control the image sensor to sequentially set two or more opening ranges on the light receiving surface corresponding to the illumination regions on the cornea and to sequentially capture the light receiving results of reflection component from the corneal endothelium obtained by the light receiving elements in the set opening range.

According to such an aspect, the opening range on the light receiving surface can be moved in synchronization with the movement of the illumination region of the illumination light on the cornea. Thereby, wide-field images of the corneal endothelial cell can be acquired in a short time with a highly simple configuration.

The method of controlling the corneal endothelial cell imaging apparatus according to the embodiments further includes an image synthesizing step of generating a synthetic image by synthesizing two or more images based on the light receiving results obtained by the light receiving elements in the two or more opening ranges on the light receiving surface.

According to such an aspect, Thereby, images with a wide field of view (for example, panoramic image) can be easily acquired with a highly simple configuration, without placing a burden on the subject.

The method of controlling the corneal endothelial cell imaging apparatus according to some embodiments further includes an analyzing step of obtaining information representing a state of corneal endothelial cells by analyzing the synthetic image.

According to such an aspect, highly accurate information on the corneal endothelial cell(s) can be easily provided.

A program according to some embodiments causes a computer to execute each step of the method of controlling the corneal endothelial cell imaging apparatus described in any one of the above.

According to such an aspect, the spatial light modulator and the image sensor are controlled so as to synchronize the irradiation of the illumination light onto the desired illumination region on the cornea using the spatial light modulator and the setting of the opening range on the light receiving surface corresponding to the illumination region on the cornea. This allows to image the corneal endothelial cell(s) at high speed. Further, by capturing the light receiving result of the reflection component from the corneal endothelium obtained by the light receiving element in the set opening range, the reflection component from the corneal endothelium can be efficiently received with a simple configuration, without being affected by unnecessary reflection component (e.g., the reflection component from the corneal epithelium). Therefore, high quality images of the corneal endothelial cell can be acquired easily.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the method of controlling the corneal endothelial cell imaging apparatus is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A corneal endothelial cell imaging apparatus, comprising:
an irradiation system including a spatial light modulator modulating light from a light source, and configured to irradiate slit-shaped illumination light toward a cornea of a subject's eye by modulating the light from the light source using the spatial light modulator;
a light receiving system arranged obliquely to the irradiation system and including an image sensor receiving reflected light from the cornea; and
a controller configured to control the spatial light modulator so as to irradiate the illumination light onto an illumination region on the cornea, and configured to control the image sensor to set an opening range on a light receiving surface corresponding to the illumination region on the cornea and to capture a light receiving result of reflection component from a corneal endothelium obtained by a light receiving element in the set opening range.

2. The corneal endothelial cell imaging apparatus of claim 1, wherein
the controller is configured to control the spatial light modulator so as to sequentially irradiate the illumination light onto two or more illumination regions on the cornea, and is configured to control the image sensor to sequentially set two or more opening ranges on the light receiving surface corresponding to the illumination regions on the cornea and to sequentially capture the light receiving results of reflection component from the corneal endothelium obtained by the light receiving elements in the set opening range.

3. The corneal endothelial cell imaging apparatus of claim 2, further comprising
an image synthesizer configured to generate a synthetic image by synthesizing two or more images based on the light receiving results obtained by the light receiving elements in the two or more opening ranges on the light receiving surface.

4. The corneal endothelial cell imaging apparatus of claim 3, further comprising
an analyzer configured to obtain information representing a state of corneal endothelial cells by analyzing the synthetic image.

5. The corneal endothelial cell imaging apparatus of claim 1, wherein
the irradiation system includes a slit in which an aperture is formed, the slit being configured to be irradiated by the light from the light source, and
the spatial light modulator includes an optical scanner configured to deflect the slit-shaped illumination light passing through the aperture formed in the slit.

6. The corneal endothelial cell imaging apparatus of claim 5, wherein
the slit is arranged at a position substantially conjugate optically to the corneal endothelium.

7. The corneal endothelial cell imaging apparatus of claim 5, wherein
the optical scanner is arranged at a position substantially conjugate optically to the light source.

8. The corneal endothelial cell imaging apparatus of claim 5, further comprising
a first relay lens system arranged between the light source and the slit; and
a second relay lens system arranged between the slit and the optical scanner, wherein the light source is arranged at a front focal position of the first relay lens system, and
the slit is arranged at a front focal position of the second relay lens system.

9. A method of controlling a corneal endothelial cell imaging apparatus including:
an irradiation system including a spatial light modulator modulating light from a light source, and configured to irradiate slit-shaped illumination light toward a cornea of a subject's eye by modulating the light from the light source using the spatial light modulator; and
a light receiving system arranged obliquely to the irradiation system and including an image sensor receiving reflected light from the cornea, the method comprising:
an irradiation system control step of controlling the spatial light modulator so as to irradiate the illumination light onto an illumination region on the cornea; and
a light receiving system control step of controlling the image sensor to set an opening range on a light receiving surface corresponding to the illumination region on the cornea and to capture a light receiving result of reflection component from a corneal endothelium obtained by a light receiving element in the set opening range.

10. The method of controlling the corneal endothelial cell imaging apparatus of claim 9, wherein
the irradiation system control step is performed to control the spatial light modulator so as to sequentially irradiate the illumination light onto two or more illumination regions on the cornea, and
the light receiving system control step is performed to control the image sensor to sequentially set two or more opening ranges on the light receiving surface corresponding to the illumination regions on the cornea and to sequentially capture the light receiving results of reflection component from the corneal endothelium obtained by the light receiving elements in the set opening range.

11. The method of controlling the corneal endothelial cell imaging apparatus of claim 10, further comprising
an image synthesizing step of generating a synthetic image by synthesizing two or more images based on the light receiving results obtained by the light receiving elements in the two or more opening ranges on the light receiving surface.

12. The method of controlling the corneal endothelial cell imaging apparatus of claim 11, further comprising
an analyzing step of obtaining information representing a state of corneal endothelial cells by analyzing the synthetic image.

13. The method of controlling the corneal endothelial cell imaging apparatus of claim 9, wherein
the irradiation system includes a slit in which an aperture is formed, the slit being configured to be irradiated by the light from the light source, and
the spatial light modulator includes an optical scanner configured to deflect the slit-shaped illumination light passing through the aperture formed in the slit.

14. The method of controlling the corneal endothelial cell imaging apparatus of claim 13, wherein
the slit is arranged at a position substantially conjugate optically to the corneal endothelium.

15. The method of controlling the corneal endothelial cell imaging apparatus of claim 13, wherein
the optical scanner is arranged at a position substantially conjugate optically to the light source.

16. The method of controlling the corneal endothelial cell imaging apparatus of claim 13, wherein
the corneal endothelial cell imaging apparatus further includes:
a first relay lens system arranged between the light source and the slit; and
a second relay lens system arranged between the slit and the optical scanner, wherein
the light source is arranged at a front focal position of the first relay lens system, and
the slit is arranged at a front focal position of the second relay lens system.

17. A non-transitory computer readable recording medium storing a program of causing a computer to execute each step of the method of controlling the corneal endothelial cell imaging apparatus of claim 9.

* * * * *